United States Patent
Simons et al.

[11] Patent Number: 6,071,294
[45] Date of Patent: Jun. 6, 2000

[54] LANCET CARTRIDGE FOR SAMPLING BLOOD

[75] Inventors: Tad Decatur Simons, Palo Alto; Michael Greenstein, Los Altos; Dominique Freeman, Pescadero; Leslie Anne Leonard, Portola Valley; David A. King, Menlo Park; Paul Lum, Los Altos, all of Calif.

[73] Assignee: Agilent Technologies, Inc., Palo Alto, Calif.

[21] Appl. No.: 08/985,384

[22] Filed: Dec. 4, 1997

[51] Int. Cl.⁷ .................................................. A61B 5/00
[52] U.S. Cl. ............................................. 606/181; 606/181
[58] Field of Search .................................. 606/167, 181, 606/182; 600/583, 565, 584, 564

[56] References Cited

U.S. PATENT DOCUMENTS

| | | |
|---|---|---|
| 2,061 | 4/1841 | Osdel . |
| 55,620 | 6/1866 | Capewell . |
| 1,135,465 | 4/1915 | Pollack . |
| 3,030,959 | 4/1962 | Grunert .................................. 128/329 |
| 3,358,689 | 12/1967 | Higgins .................................. 128/329 |
| 4,139,011 | 2/1979 | Benoit et al. .......................... 128/329 |
| 4,190,420 | 2/1980 | Covington et al. ..................... 422/63 |
| 4,203,446 | 5/1980 | Hofert et al. ........................... 128/329 |
| 4,207,870 | 6/1980 | Eldridge ................................. 128/766 |
| 4,230,118 | 10/1980 | Holman et al. ........................ 128/314 |
| 4,440,301 | 4/1984 | Intengan ................................. 206/456 |
| 4,442,836 | 4/1984 | Meinecke et al. ..................... 128/314 |
| 4,449,529 | 5/1984 | Burns et al. ............................ 128/314 |
| 4,469,110 | 9/1984 | Slama ..................................... 128/770 |
| 4,535,769 | 8/1985 | Burns ..................................... 128/314 |
| 4,577,630 | 3/1986 | Nitzsche et al. ....................... 128/314 |
| 4,627,445 | 12/1986 | Garcia et al. ........................... 600/583 |
| 4,712,548 | 12/1987 | Enstrom ................................. 128/314 |
| 5,133,730 | 7/1992 | Biro et al. .............................. 606/182 |
| 5,196,025 | 3/1993 | Ranalletta et al. ..................... 606/182 |
| 5,318,583 | 6/1994 | Rabenau et al. ....................... 606/182 |
| 5,318,584 | 6/1994 | Lange et al. ........................... 606/181 |
| 5,510,266 | 4/1996 | Bonner et al. .......................... 436/43 |
| 5,518,006 | 5/1996 | Mawhirt et al. ....................... 128/770 |
| 5,571,132 | 11/1996 | Mawhirt et al. ....................... 606/167 |
| 5,613,978 | 3/1997 | Harding ................................. 606/181 |
| 5,632,410 | 5/1997 | Moulton et al. ........................ 221/79 |
| 5,680,872 | 10/1997 | Sesekura et al. ...................... 600/573 |
| 5,682,233 | 10/1997 | Brinda ................................... 600/583 |
| 5,714,390 | 2/1998 | Hallowitz et al. ..................... 436/526 |
| 5,801,057 | 9/1998 | Smart et al. ............................. 436/68 |

FOREIGN PATENT DOCUMENTS

| | | | |
|---|---|---|---|
| 0254246 | 1/1988 | European Pat. Off. | ........ G01N 21/03 |
| 0630609A2 | 12/1994 | European Pat. Off. | ........... A61B 5/14 |
| WO86/05966 | 10/1986 | WIPO | ............................ A61B 10/00 |
| WO93/00044 | 1/1993 | WIPO | ............................ A61B 17/32 |
| WO98/24366 | 6/1998 | WIPO | ............................. A61B 5/14 |

OTHER PUBLICATIONS

Glucometer Elite®, "Diabetes Care System", User's Guide (Product), PP. (3 pages), Miles Inc. Elkhart, IN 1994.

*Primary Examiner*—Cary O'Connor
*Assistant Examiner*—Pamela Wingood

[57] ABSTRACT

A cartridge for sampling and analyzing blood from the skin of a patient. The cartridge has a cartridge case, a lancet, and associated with the cartridge case an analytical region for analyzing the property of blood. The lancet has a tip for lancing the skin and is housed in the cartridge case. The lancet is operatively connected to the cartridge case such that the lancet can be pushed to extend its tip outside the cartridge case for lancing the skin to yield blood. The blood from the lancing wound is transferred to the analytical region and be analyzed.

32 Claims, 8 Drawing Sheets

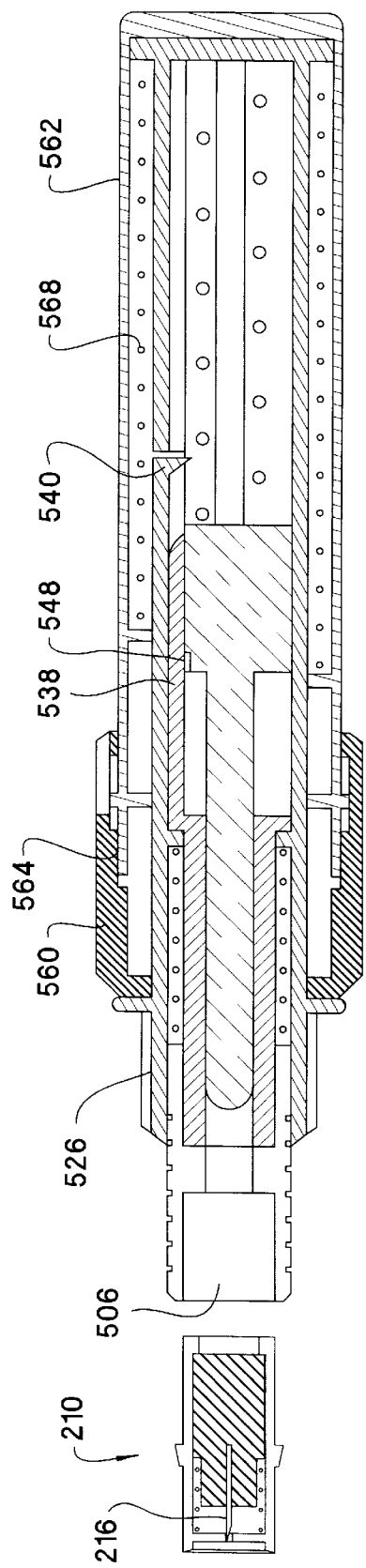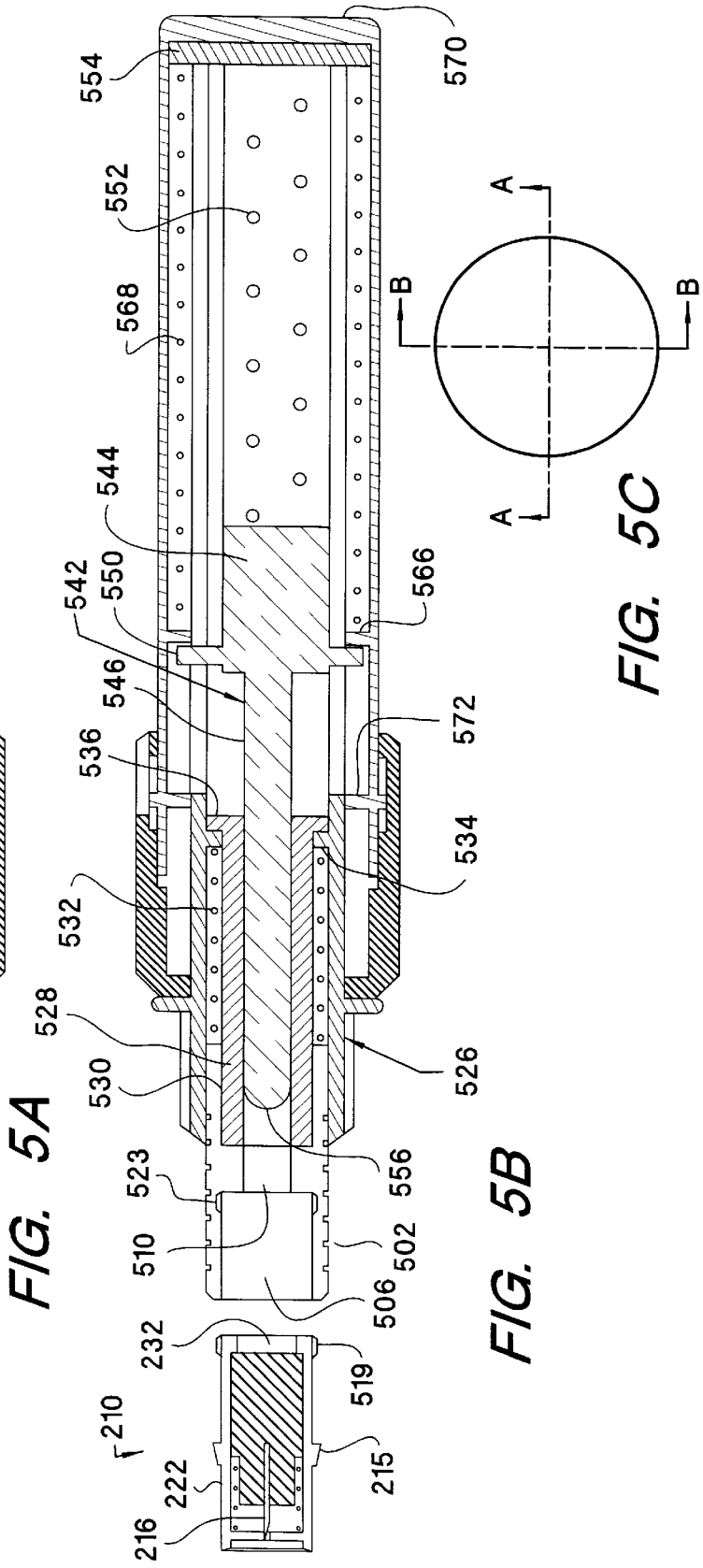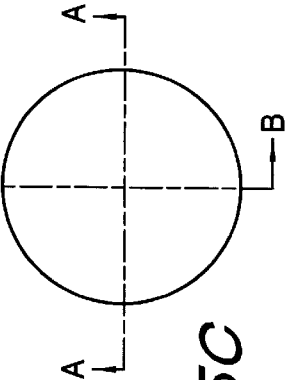

LANCET CARTRIDGE FOR SAMPLING BLOOD

FIELD OF THE INVENTION

The present invention relates to techniques for obtaining and analyzing blood samples, and more particularly to techniques that can be self-administered by a patient for obtaining and analyzing blood samples with a lancet in a convenient manner.

BACKGROUND

The analysis and quantification of blood components is an important diagnostic tool for better understanding the physical condition of a patient. Since adequate noninvasive blood analysis technology is not currently available, blood samples still need to be obtained by invasive methods from a great number of patients every day and analyzed. A well known example of such needs is self monitoring of glucose levels by a diabetic individual, e.g., performed at home. Many products for self monitoring of blood glucose levels are available commercially. Upon doctors' recommendations and using such products, patients typically measure blood glucose level several (3–5) times a day as a way to monitor their success in controlling blood sugar levels. For many diabetics, the failure to test blood glucose regularly may result in damage to tissues and organs, such as kidney failure, blindness, hypertension, and other serious complications. Nevertheless, many diabetics do not measure their blood glucose regularly. One important reason is that the existing monitoring products may be complicated, inconvenient, and painful, requiring a pinprick every time a measurement is made. Furthermore, these products require some skill, dexterity, and discipline to obtain useful measurements.

Today, a diabetic patient who needs to monitor and control blood glucose levels typically carries the following paraphernalia: (1) a supply of disposable lancets, (2) a reusable lancing device which accepts the lancets, (3) an electronic glucose meter (glucometer), (4) a supply of disposable glucose test strips for the meter, and (5) tools for insulin injection (insulin, disposable hypodermic needles, and a syringe). These items may be carried in the form of a kit, which may also contain (6) a variety of control and calibration strips to assure the accuracy of the meter and the measurement. Examples of devices for monitoring blood glucose include GLUCOMETER ELITE glucose meter, Miles Inc. Elkhart, Ind., and ONE TOUCH PROFILE glucose meter, Lifescan Inc., Milpitas, Calif.

Using a typical glucose meter and lancing device, the sampling and measurement process is generally as follows. First, the user prepares the meter for use by removing a test strip from a protective wrapper or vial and inserting the test strip in the meter. This simple process requires some dexterity, since the test strips are very small, flexible, and can be damaged by accidentally touching the active sensing region. The glucose meter may confirm the proper placement of the test strip and indicate that it is prepared for a sample. Some glucose meters also may require a calibration or reference step at this time. Next, the patient cleans his finger when he intends to use the lancet-the finger is the preferred place for routine sampling, because it is an easily accessible place for most people. The user prepares the lancing device by (1) removing a cover from the lancing device, (2) placing a disposable lancet in the lancing device, (3) removing a protective shield from the sharp lancet tip, (4) replacing the cover, and (5) setting a spring-like mechanism in the lancing device which provides the force to drive the lancet into the skin. These steps may happen simultaneously, e.g., typical lancing devices set their spring mechanisms when one installs the lancet. The user then places the lancing device on the finger. (The density of nerve endings decreases toward the lateral edges of the fingertips; thus, slightly lateral locations are preferred to the fingertips.) After positioning the lancing device on the finger, the user presses a button or switch on the device to release the lancet. The spring drives the lancet forward, creating a small wound.

After lancing, a small droplet of blood may appear spontaneously at the lancing site, usually 2–20 $\mu$l in volume. If no blood sample appears spontaneously, the patient may "milk" the finger by massaging or squeezing it slightly and thereby promoting blood flow from the wound. In either case the user examines the droplet of blood, judges by eye and experience whether the size of the sample is adequate for the chosen test strip (different test strips require different sample volumes). If adequate, the user quickly places the blood sample on a test strip (held in the glucose meter) according to manufacturer's instructions. Typically, the user inverts the finger to create a pendant drop and touches the drop (not the finger) to an active region on the test strip that absorbs the blood. The action is difficult because inverting the finger over the test strip occludes the view of both the drop and the active region of the test strip. Furthermore, it is difficult to control the separation between the finger and the test strip which may be only a millimeter. Certain types of strip may require blotting and rubbing in a particular way. Another type of test strip draws the sample into the active region by capillary action. With this type, the user brings the sample in contact with a small opening on the test strip, and capillary action draws the sample volume into the test strip. Both types of strips (absorbent blots and capillaries) require that adequate sample volumes of blood exist on the finger before transferring the sample to the strip. One cannot apply more drops after the first application. This is because the principle of glucose measurement methods using current glucose meters depends on the rate of change in a chemical reaction, and the addition of additional sample confounds that rate and thus the calculation of glucose concentration. For convenience to the patient (user), it is desirable to have the entire droplet wick away from the finger onto the test strip, leaving the finger mostly free of blood. This is easier to accomplish with the capillary-fill test strips. The GLUCOMETER ELITE device has capillary-fill type test strips which require a few microliters of sample, only some fraction of which contacts the active sensor region.

After blood has been transferred to the test strip, the glucose meter then measures the blood glucose concentration (typically by chemical reaction of glucose with reagents on the test strip). Such blood glucose measurements permit the diabetic to manage his glucose levels, whether that be to inject a corresponding dose of insulin (generally Type I diabetic) or using a protocol established with his physician to modify his diet and exercise (Type I or Type II diabetic). Used lancets and test strips are removed and discarded (or kept for subsequent disposal in a hazardous waste container kept elsewhere). Any extra blood is cleaned from the equipment and the wound site, and all pieces of apparatus are stored for future use. The entire process usually takes a few minutes.

With the currently available blood glucose monitoring technology, a new lancet and test strip are used every time. The lancet and test strip are separate items, often purchased from different manufacturers. Furthermore, both are protected by a package or a protective shield, which must be removed before use, adding the requirement for dexterity. Because both are exposed to blood (considered a bio-hazard) they require careful or special disposal.

Each lancet prick causes pain. Among other considerations, pain from the lancet corresponds to the size of the wound, for a given location on the finger. A small lancet wound, which may cause less pain, may not provide enough blood for a sample, while a large wound may produce considerable pain and may clot slowly, causing great inconvenience to the user, who must take great care not to smear the leaking blood everywhere—clothes, work surfaces, glucometer, etc.—for some time thereafter.

From the above, it is clear that the conventional technique for blood sampling and analysis requires dexterity. Dexterity is required to load strips in a glucometer (unwrapping and inserting), as well as for positioning a small droplet onto the sensor surface of a test strip. Sample droplets are a few millimeters across and must be placed on similarly sized area of the test strip. This can be especially difficult for a weak, chronic or elderly diabetic patient, whose motions may be unsteady, vision compromised, or judgment impaired. Thus, the above prior systems are inconvenient and unpleasant to use. These shortcomings reduce the level of compliance of patients who need to perform these measurements assiduously.

Therefore, it is desirable to devise techniques of blood extraction and measurement that are easy to administer. What is needed are improved devices and methods for sampling and analyzing blood that are simple to perform and easy to use for any patient population.

SUMMARY

This invention provides techniques for extracting a sample of human blood for the measurement of one or more of its constituents, for example, as might be used for routine monitoring of a chronic condition such as diabetes. The techniques of the present invention simplify the extraction and transfer of the blood sample, and reduce the unpleasantness and inconvenience of the process. The techniques can be advantageously used in, for example, blood glucose monitoring as explained above.

In one aspect of the present invention, an improved blood sampling apparatus is provided. The apparatus includes a cartridge. An embodiment of the cartridge includes a cartridge case and a lancet. The lancet has a sharp tip for piercing the skin and is operatively connected for motion to the cartridge case in which it is housed. The tip can be made to extend outside the cartridge case for lancing the skin to yield blood. In an embodiment, associated with the cartridge case is an analytical region for sensing the property of blood. In another embodiment, a compartment can be present in the cartridge to store blood for analysis at a later time.

In an embodiment of the present invention, the technique of sampling blood utilizes a single unit for lancing and measurement (versus separate lancers and meters as in methods in prior technology) to significantly reduce the assortment of devices and supplies the user must carry. The lancet and the analysis site for blood are in the same test cartridge, further improving the convenience of use. Using the blood sampling and analysis devices of the present invention, unlike the procedures in prior technology, the long list of steps required is significantly reduced. For example, there is no need to remove separately the lancet from its protective shield and to remove a test strip from its protective packaging. The need for handling a lancet actuating device separate from the glucometer is obviated. Further, the act of inserting the test cartridge into the glucometer in the present invention is significantly simpler than prior methods of preparing a glucose meter for use. In fact, in a preferred embodiment of the present invention, the process of sampling and analyzing blood from a finger (not including the steps for cleaning the finger before sampling blood) is reduced to inserting a test cartridge into the glucometer, moving a test cartridge into position, cocking the actuator and releasing it to prick the finger, turning the finger to put the blood droplet to the sample port, and pushing the right buttons to control the electronics of the glucometer. All these steps can be performed from start to finish without having to put down the glucometer and pick up another device, which is impossible with prior techniques. This advantage is particularly beneficial to the sight impaired.

BRIEF DESCRIPTION OF THE DRAWINGS

The following figures are included to better illustrate the embodiments of the apparatus and technique of the present invention. In these figures, like numerals represent like features in the several views.

FIG. 5A shows a sectional view of a blood sampling-analysis device suitable for used with a bar-shaped test cartridge in accordance with the present invention, FIG. 5B shows a sectional view of the blood sampling-analysis device of FIG. 5A taken on a sectional plane of at a right angle thereto.

FIG. 5C shows a schematic cross-section relating the sectional views of FIGS. 5A and 5B.

DETAILED DESCRIPTION OF THE INVENTION

In one aspect of the invention, the present invention provides an apparatus—device having a lancet within a cartridge that facilitates sampling blood safely, and preferably analyzing the blood sample conveniently. Using the device, a patient can obtain a blood sample, and dispose of the cartridge without touching the lancet by hand. In a preferred embodiment, analysis of the blood can be done in the cartridge.

Cartridges

A preferred embodiment of a cartridge of the present invention includes a lancet, a cartridge case with an opening through which the lancet can protrude, and a test area associated with the cartridge case for analysis of blood. The lancet is mounted in the cartridge case in such a manner that (1) it can move with respect to the cartridge case and extend through the opening when forced by a separate actuator, and (2) when no actuating force acts on the cartridge, the lancet has a natural resting position completely encased inside the cartridge case. Analysis can be done in the test area (i.e., analytical region). An alternative is that a chamber can be used to store blood to be transferred to a separate analytical area from the test area. It is to be understood that although test cartridges with analytical regions are described in detail herein, the cartridges of the present invention also include cartridges that do not have an analytical region, such as a cartridge having a chamber for storing blood after sampling. Such storage cartridges, whether the flat type or the bar-shaped type (which will be described below), will be obvious to a person skilled in the art in view of the present disclosure. One example would be a cartridge having a storage chamber connected by a channel to the blood inlet port in the afore-mentioned test cartridges, without the reagents that can interact with the blood. Further, it is to be understood that the cartridges of the present invention may be applicable for other types of actuators for driving the cartridges, and that other variations of the cartridges can be made to be used with the driving mechanisms described herein.

Flat Cartridge

Figure 1A:
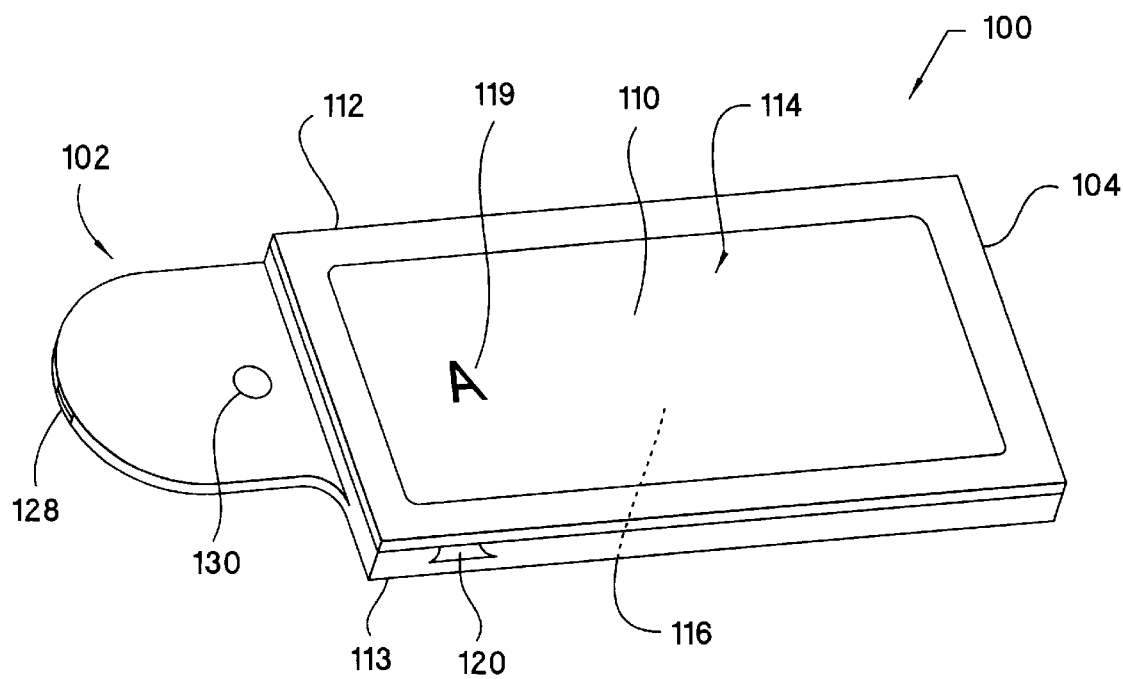
FIG. 1A shows an isometric view of an embodiment of the flat type of test cartridge of the present invention.
Figure 1B:
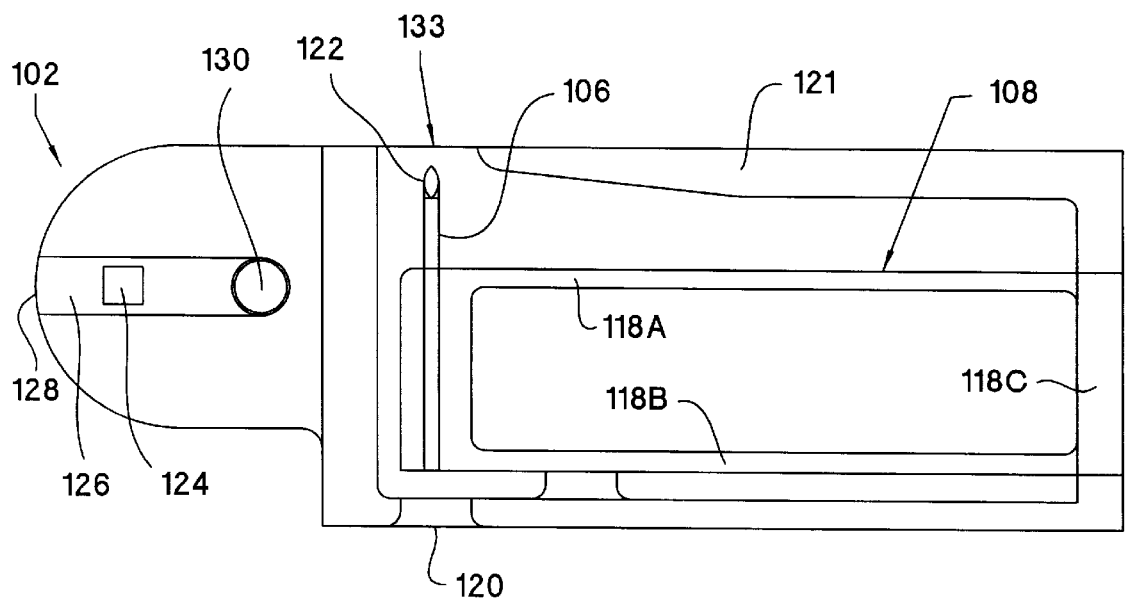
FIG. 1B shows a plan view of the test cartridge of FIG. 1A.

FIG. 1A shows an isometric view and FIG. 1B shows a plan view of an embodiment of a test cartridge that can be stacked in storage. According to the present invention, the test cartridge of FIG. 1A and FIG. 1B has a generally flat appearance, thus allowing many test cartridges to be stacked together for storage, e.g., in the cassette of cartridges. However, it is to be understood that other non-flat-shaped cartridges can also be used, so long as they can be stacked. For example, the cartridge can have two opposite surfaces each having a cross section that is curved, wavy, etc. to match the other surface. A test portion 102 protrudes from one side of the test cartridge 100. The test cartridge 100 may include a material for analysis of blood (see infra). The device 100, which in the present embodiment has analytical capability, is referred to as a "test cartridge" because strips for analysis of blood in prior glucose meters are called "test strips" in the technical field. The test cartridge 100 has a cartridge case 104 connected with the test area 102. A lancet 106 is connected to a cantilever lancet frame 108. The side 118C of the cantilever lancet frame 108 remote to the lancet 106 is affixed to the cartridge case 104 whereas the side of the cantilever frame 108 near the lancet 106 is not affixed to the cartridge case 104. Thus, the lancet is operatively connected in the cartridge case 104 for movement. A covering 110 which has an absorbent material (for absorbing residual blood from the wound after lancing and testing and which could contain alcohol for cleaning) covers a surface (preferably the top surface) of the cartridge case 104. As used herein, the term "top surface" when used in connection with the generally flat test cartridge refers to the surface that is exposed for the most convenient access when the test cartridge is installed in association with a driver for lancing, e.g., to allow identification marks on the test cartridge to be seen. Preferably, the top surface will face the same direction as displays of a glucometer when the test cartridge is loaded (or deployed) in the glucometer. Preferably, the cartridge case has a top face 114 on a top plate 112 and a bottom face 116 on a bottom plate 113 that are generally flat such that cartridges of this kind can be stacked one on top of another, and such that the covering material 110 can be conveniently used for wiping blood from the skin after lancing.

In this embodiment, as shown in FIG. 1B, the lancet 106 is mounted on a two-armed cantilever frame 108, the arms 118A, 118B of the cantilever frame 108 being about 20 mm long. A separate mechanism (e.g., an actuator rod not shown in the figures) inserted through a push port (or access hole) 120 can push the lancet 106 forward by acting against the part of the cantilever frame near the blunt end of the lancet 106. The lancet 106 at its distal end (remote from the proximal, attached end) has a sharp tip 122 for penetrating the skin. As used herein, the term "distal" refers to a location or direction towards the skin during lancing. The term "proximal" refers to a location or direction that is opposite to "distal," near to the end of the lancet that is attached to the cantilever frame. The cantilever structure causes the lancet 106 to move in a generally straight direction (parallel to the lancet axis) with negligible curving or non-linear motion, in order to pierce the skin with minimal tearing. In an at-rest state the lancet 106 resides about 0.5 mm proximal of the outside surface of the cartridge to prevent unwanted injuries. Although a larger lancet can be used if desired, the lancet 106 is preferably 0.35 mm in diameter or smaller in order to not inflict a large wound.

The cartridge case 104 has a port 120 on the side of the cartridge case near to the blunt end of the lancet 106 for an actuator arm or rod (e.g., a push rod) to be inserted to push the lancet, thereby extending the lancet tip out the cartridge case 104. When pushed, i.e., actuated, the lancet 106 extends through the cartridge wall through an exit port 133. The lancet 106 will extend out of the side of the lancing device through lancing hole 176, see FIG. 4. The cantilever arms 118A and 118B have a resilient property that, when the cantilever arms are bent, a tension develops to return (or spring) the lancet 106 to its at-rest position after lancing the skin and the actuating force on the lancet 106 is withdrawn (e.g., the actuator rod that inserts into the port 120 withdraws). The maximal total travel of the lancet may be a few millimeters, limited by the interference (contact) of the cantilever lancet frame 108 and cartridge wall 121. The exact limit of travel of the lancet, which is important to minimize pain and injury, may be controlled by a mechanism which pushes the cartridge frame (which will be described later in the following). Each cartridge 100 may have an identifying mark 119 on the top surface 114 or absorbent cover 110 or in a non-test area on the test portion 102. The identifying mark 119 can indicate the number of the cartridge (in a batch) or a special function (e.g., for a calibration cartridge). Further, special function cartridges can have a different color. These identifying marks would be preferably large to assist the sight-impaired.

FIG. 1B is a plan view of the cartridge showing the test portion 102 and the lancet structure. The test portion 102 includes a test compartment (or test area) 124 depicted as a small square. As used here, the term "test compartment" refers to a space into which blood can pass and which may lead to the area where the property of the blood is sensed. A capillary passageway 126, for example, allows communication between a port (or entrance) 128 from which blood enters the test area 124. Either this passageway or the entire area (102) may be clear to aid the visually-impaired to see that the sample area fills appropriately. A vent hole 130 a distance (e.g., about 5 mm) away from the entrance 128 to the capillary, to the opposite side of the test area 124, terminates the capillary force to halt the filling of the capillary volume after pulling a blood sample over the active test area 124. As an alternative, a compartment without analytical capability can be used in place of a test area for storing blood. Such a compartment may have anticoagulants to prevent the blood from clotting and to prepare the blood for testing. Preferably, the wall surrounding the compartment 124 as well as the capillary passageway 126 is made of a transparent material so that they are optically accessible to allow the content to be seen by the user.

Figure 1C:
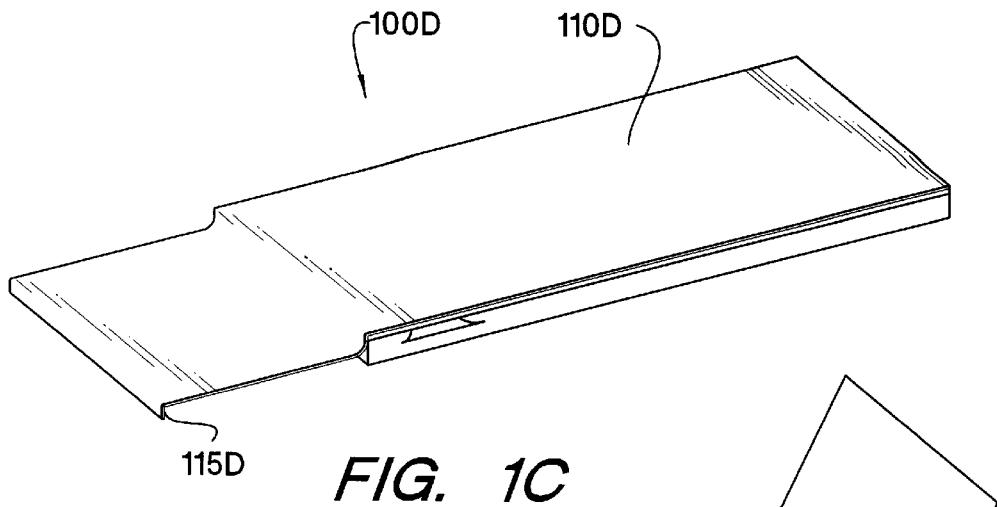
FIGS. 1C to 1E shows isometric views of an embodiment of a test cartridge of the present invention having a protective cover being peeled back.
Figure 1D:
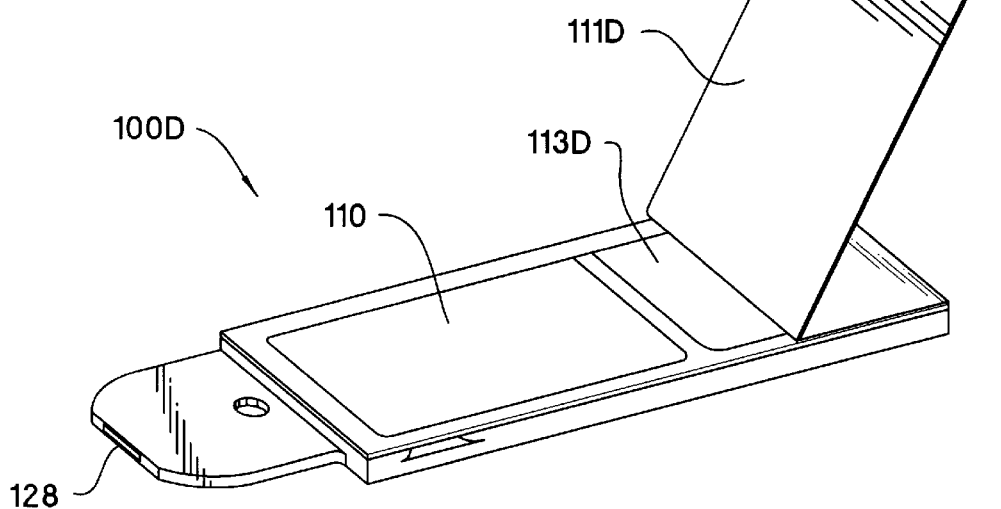
Figure 1E:
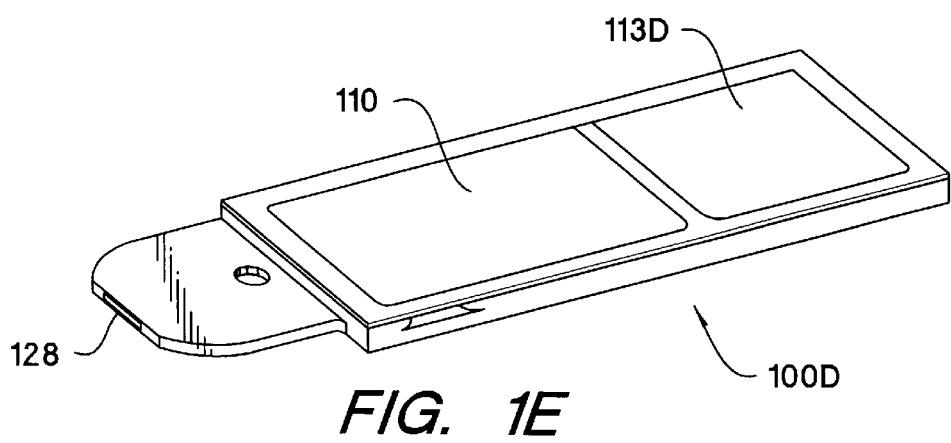

The cartridge may also contain an area for warming the user's lancing site (e.g., the skin of a finger) prior to blood drawing. Such cartridges are particularly useful for the person who has reduced peripheral circulation. FIGS. 1C to 1E shows an embodiment of a cartridge 100D having a heating pad 113D adjacent to the test area 129 and the absorbent material. The heating pad can contain chemicals that react exothermically when exposed to air without combustion. The exothermic reaction can be initiated by peeling a cover (tape) 111D off the heating pad 100D, exposing the heating pad to air (see FIGS. 1D and 1E). The ratio of chemical reagents can be adjusted such that the amount of heat generated is not excessive to avoid burning the user. An overlaying material such as a fabric distributes the heat and allows a person to keep his finger on the pad for variable amounts of time to control the comfort level of warming.

Reagents that react with air to produce heat are known in the art. This type of reaction is currently exploited in, e.g., the "WARM PACK" warming product, sold by Grabber Mycoal Co., Concord, Calif. This product contains an iron metal powder, water, and a sulfate or chloride salt. The iron is the source of heat generated by the iron contacting the salt in the presence of the water. Fillers are added as wetting agents and to provide a water-retention medium. When the outer plastic wrapping is removed, the inner packet is exposed to air and generates significant warmth, from 40° C. to 60° C., for up to several hours.

Preferably, the cover 111D covers the top surface of the cartridge 100D so that any opening in the test portion 102 and absorbent pad 110 that will be exposed to the lancing site can be kept sterile until the cover 111D is peeled off. The cover 110D can also cover the lancing hole 176 (not shown in FIG. 1C). A flap 115D on the cover 110D allows the user to grip it and peel back to expose the sample port 128, the absorbent pad 110 and the heating pad 113D, as well as the lancing hole 176, if desired. The placement under the absorbent material protects the skin from direct contact with the warming element which locally may be excessively warm. Alternatively, the warming mechanism could be located on the glucometer and run electrically or by batteries.

In a preferred embodiment (although not shown in FIG. 1), the test cartridge 100 has electrical contacts that allow for electrical communication with an instrument that processes a measurement (and perhaps controls the sensing) of an analyte (e.g., glucose) on the active test area. Such electrical contacts can be placed at a variety of locations on the test cartridge. Placing the contacts on the bottom (i.e., the side opposite from the covering 110 permits a simple design and a simple interface to an instrument.

For analysis of the blood sampled, the test area 124, or the passageway 126 leading to it, can contain chemicals that react with components of the blood samples. For example, enzymes that react with glucose can be present. The test area may also contain reagents that react with the iron present in the blood hemoglobin. Techniques, including electrochemical or spectroscopic techniques, that can be used for analysis of blood can be incorporated in the test cartridge 100. Examples of applicable analysis techniques can be found in, e.g., Tietz, Norbert W., Textbook of Chemical Chemistry, Chapter 6, pp 784–807, W. B. Saunders Co., Philadelphia, Pa., 1986, which are incorporated by reference herein. Test strips for analyzing glucose, pH, iron, and other common blood qualities are known in the art. For example, ONE TOUCH PROFILE diabetes tracking system commercially available from Lifescan Inc., Milpitas, Calif. 95035 has a unit that utilizes a strip for analyzing blood glucose and has an electronic system for displaying the result of analysis.

Other embodiments of test cartridges are also applicable in accordance with the present invention, such as one with the test area 124 protruding at a different side of the lancet area, or having a test area that resides directly neighboring the lancet 106 near the recessed tip 122, so that the entrance (i.e., sample port) 128 to the capillary passageway 126 and the exit port 133 for the lancet 106 are nearly coincident. This latter design enables the patient to lance the skin, and have the sample port for the test strip co-located for immediate filling. For example, in another embodiment of a test cartridge 100B (FIGS. 2A and 2B) in which the general configuration is similar to that of FIG. 1A and FIG. 1B, the cartridge sample port 128B may be positioned near to the lancet tip 122B. This test cartridge 100B also includes a lancet 106B, cantilever arms frame 108B, cover plates 112B, 113B, absorbent cover 110B, and active test area 124B with functions similar to test cartridge 100 described above. The lancet 106B, when deployed in a glucometer and ready for lancing, can be located so that at the time of lancing, the lanced site (e.g., finger) and the sample port are nearly coincident, thereby simplifying the transfer of blood from the lancing wound to the test strip (and permitting potentially an automated or semi-automatic transfer of blood sample without action by the patient). The test area 124B can be immediately behind the lancet exit port 133B so as to allow a drop of blood the lanced skin to immediately enter the lancet exit port 133B to access the test area 124A.

The top plate 112B, or the top surface 110B may have a variety of useful markings 113B that indicate which test cartridge is in use (in the case that the test cartridge is one out of many from a stack of test cartridges), and indication of batch or lot number of manufacture (for quality control and calibration), or that the cartridge is a special-purpose cartridge (e.g., for checking or calibration). Such markings can, of course, be present also on the test cartridge of FIG. 1A and FIG. 1B. (For comparison, some current lancing systems that make use of calibration strips are, e.g., GLUCOMETER ELITE glucose meter, Miles Inc. Elkhart, Ind., and ONE TOUCH PROFILE glucose meter, Lifescan Inc., Milpitas, Calif.). An actuator port 120B is located on the side of the test cartridge 100B opposite to the lancet exit port 133B. Through the actuator port 120B an actuator can act on the lancet frame to drive the lancet, i.e., urge the lancet forward, through the lancet exit port 133B for lancing. Preferably, when blood from a lancing wound contacts the aperture of the sample port, capillary action draws in the blood spontaneously. A vent 130B on the base prevents capillary forces from drawing blood samples past the vent. The test area is located inside a test chamber between the vent and the sample port. Filling the test chamber by means of capillary forces provides a uniform sample volume and a uniform manner of filling, which helps to provide reliable test results.

An advantage of this design is that lancing and sampling occur in a single action. The improved integrated cartridge retains all the other beneficial features of the earlier invention—simple design, ability to stack into a cassette of cartridges, a wiping surface on top of the cartridge, etc. The improved cartridge design can also function in the ergonomic glucometer described in the copending U.S. patent application Docket No. 10970322-1, entitled "Integrated System and Method for Sampling Blood and Analysis" and copending U.S. patent application Docket No. 10971582-1, entitled "Reproducible Lancing for Sampling Blood," filed on the same day and commonly assigned to the same assignee as the present application, said copending applications are incorporated by reference in their entirety herein. These copending applications also described a way to adjust the depth of penetration of the lancet, which is applicable in using the cartridges of the present invention.

Figure 2A:
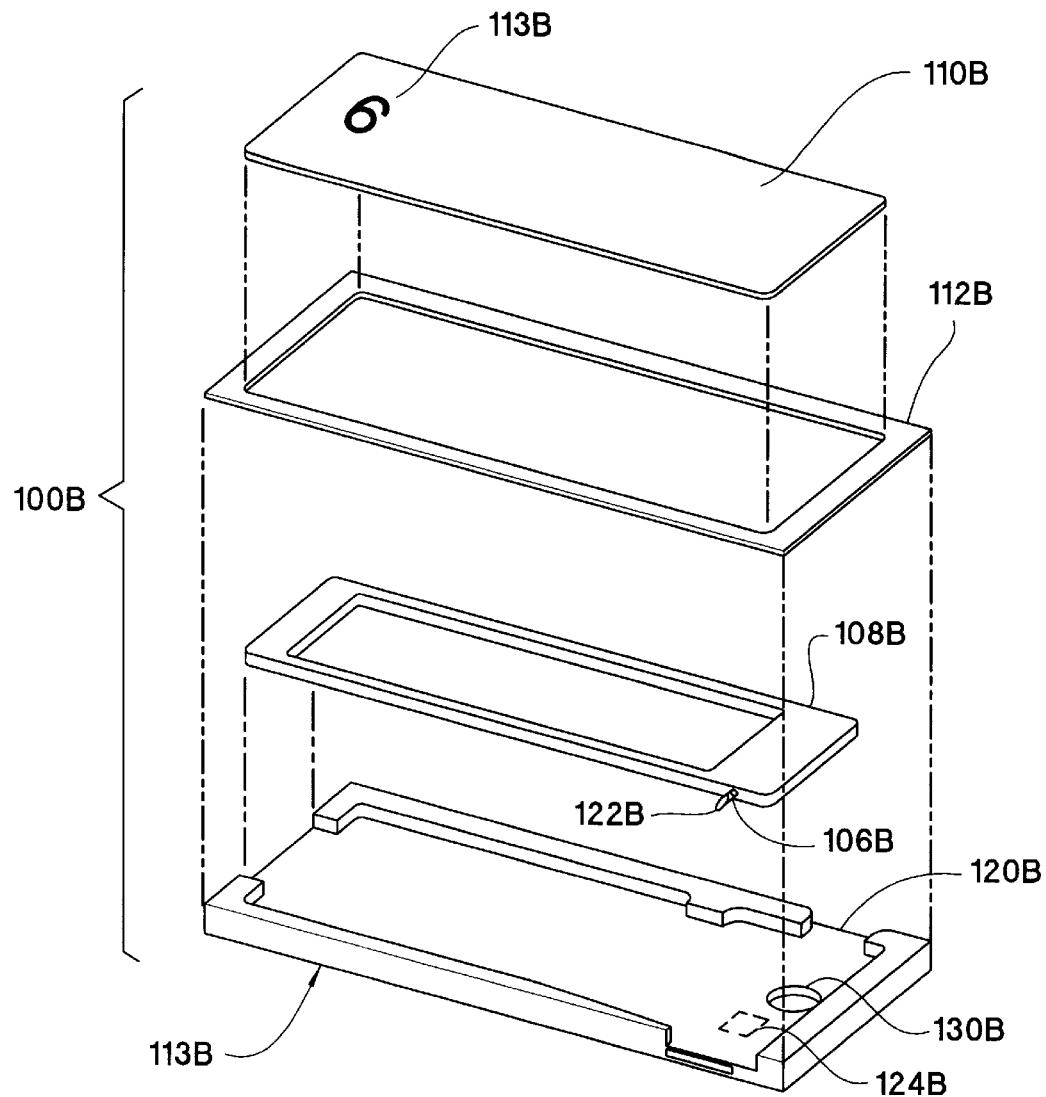
FIG. 2A shows an exploded isometric view of another flat type test cartridge of the present invention.
Figure 2B:
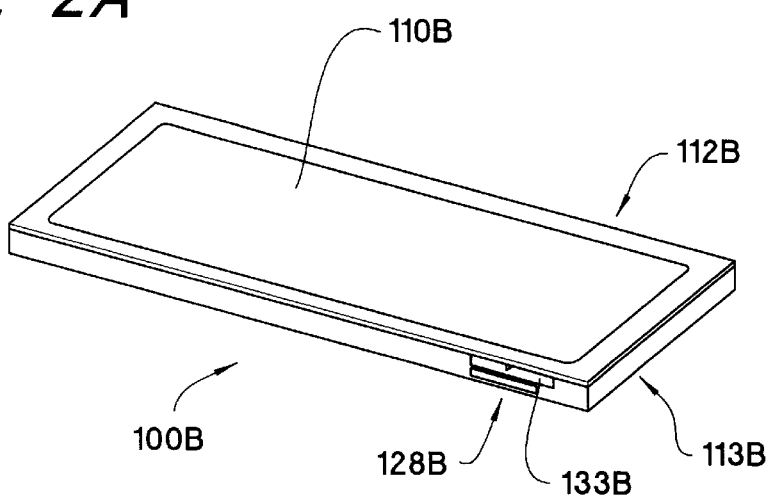
FIG. 2B shows an isometric view of the flat type test cartridge of FIG. 2A.
Figure 2C:
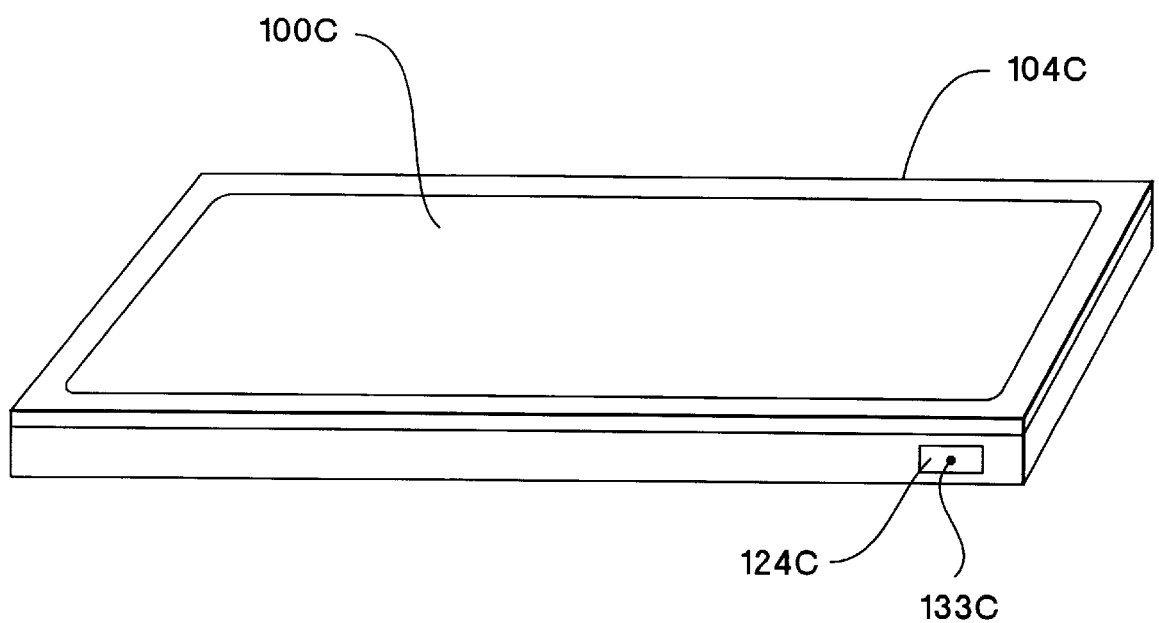
FIG. 2C shows an isometric view of yet another flat type test cartridge of the present invention.

In an alternative embodiment shown in FIG. 2C, the test cartridge 100C has a test area 124C that is at the immediate vicinity of the lancet exit port 133C, which in this embodiment is a hole. The test area 124C can be a sensing surface surrounding the lancet exit port 133C. Preferably the test area 124C is set back slightly from the distal side of the cartridge case 104C, resulting in a small void area protecting the test area 124C from inadvertent contacts with the skin or other objects. When the skin is lanced and a drop of blood appears, the drop of blood can reach beyond the set back distance to contact the test area 124C. The driver for driving the lancet in the cartridge can be similar to that for a bar-shaped cartridge, both of which will be described in detail below.

Bar-Shaped Cartridge

Figure 3A:
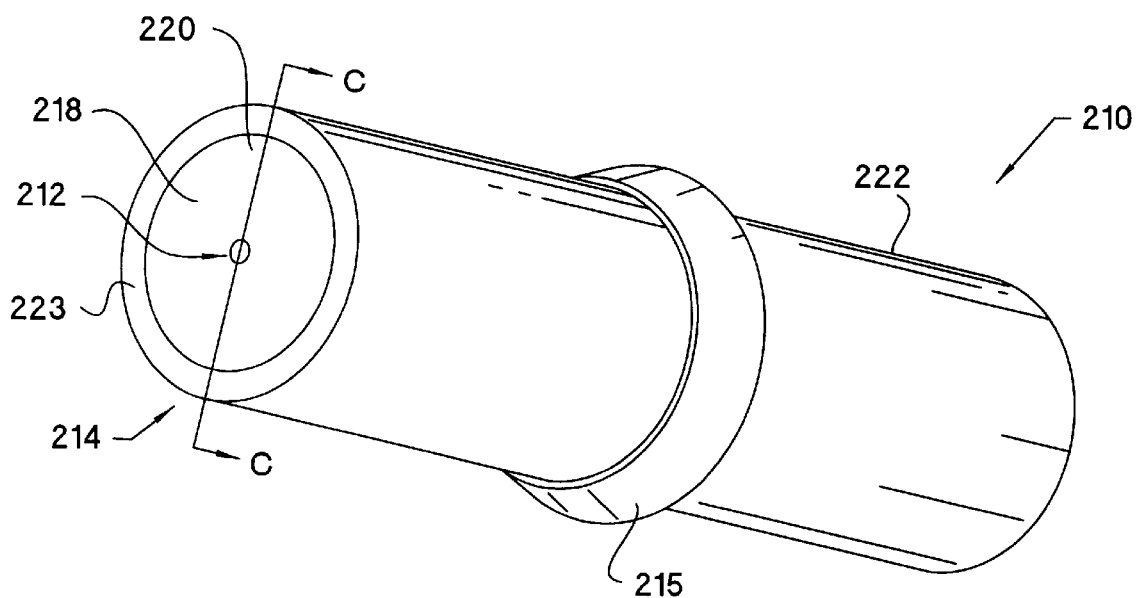
FIG. 3A shows an isometric view of a bar-shaped test cartridge of the present invention.
Figure 3B:
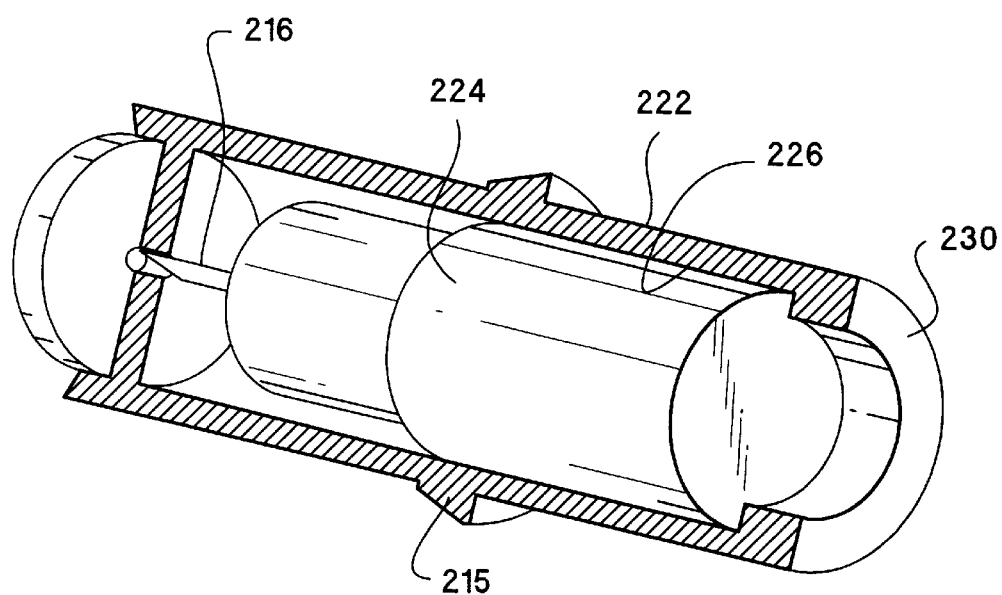
FIG. 3B shows an exploded isometric view in portion of the test cartridge of FIG. 3A.

A test cartridge does not necessarily have to have a generally flat appearance. FIGS. 3A to 3D show an embodiment of a bar-shaped test cartridge with a lancet and a blood analyzer, i.e., sensor (such as a blood chemistry test strip that can determine glucose level) and which can be mounted easily into a driving instrument (driver). The overall lancing device operates with the test cartridge to gather a blood sample in a single operation and simplifies the measurement procedure. FIG. 3A shows an isometric view of the embodiment of the test cartridge 210, about 6 mm in diameter and 15–20 mm in length. FIG. 3B shows an isometric view, cut-out in portion, of the test cartridge 210 of FIG. 3A. For comparison, the size and shape is similar to that of the ULTRAFINE lancets of the Becton-Dickinson Co. It is noted that, although the bar-shaped test cartridge 210 has, preferably, a round cross-sectional shape, it can also have other regular cross-sectional shapes, such as oval, square, rectangle, rhombus, triangle, etc. An aperture 212 (or lancet exit hole) is located at a distal end 214 of the test cartridge 210. A lancet 216 is housed at rest inside the test cartridge 210 proximal of (i.e., beneath if considering the sharp lancet tip as facing upwards) the aperture 212, which has a diameter slightly larger than the lancet 216 (~0.35 mm diameter). The lancet 216 can pass through the aperture 212 when actuated for lancing. Herein, when referred to a bar-shaped test cartridge, "top," and "up" refer to a direction or location towards the skin to be lanced, i.e., towards the distal end. The material 218 around the aperture can be an absorbent material which serves to soak up blood after lancing. The absorbent material, or the surface beneath it, can also serve as the active test area 220 for measurements of blood characteristics, such as glucose level. The test cartridge case 222 has a lip 223 protruding slightly out distally at the distal end 214. The protruding lip 223 results in a small void area protecting the test area 220 from being inadvertently touched or creating a controlled tension on the skin of the lancing site. As in existing glucose measurement techniques, a chemical reaction occurs when blood contacts the test area 220, and thus, for example, indicates the presence and amount of glucose. The test area 220 can generate an electrical signal that is conducted from the test area 220 (preferably via conductors molded into the case) to electrical contacts (not shown) on the cartridge case 222. FIG. 3B is a projected sectional view in portion of the cartridge, showing the cartridge case 222, the lancet 216, and the absorbent material 218 distal to the lancet 216 when at rest. The lancet 216 is mounted on a cylindrical lancet mount 224. The cartridge case 222 has a cylindrical internal wall 226 upon which the lancet mount 224 can slide. As used herein, the meaning of the term "compartment" when referred to the space for receiving blood also can include the space encircled by the lip 223.

Figure 3C:
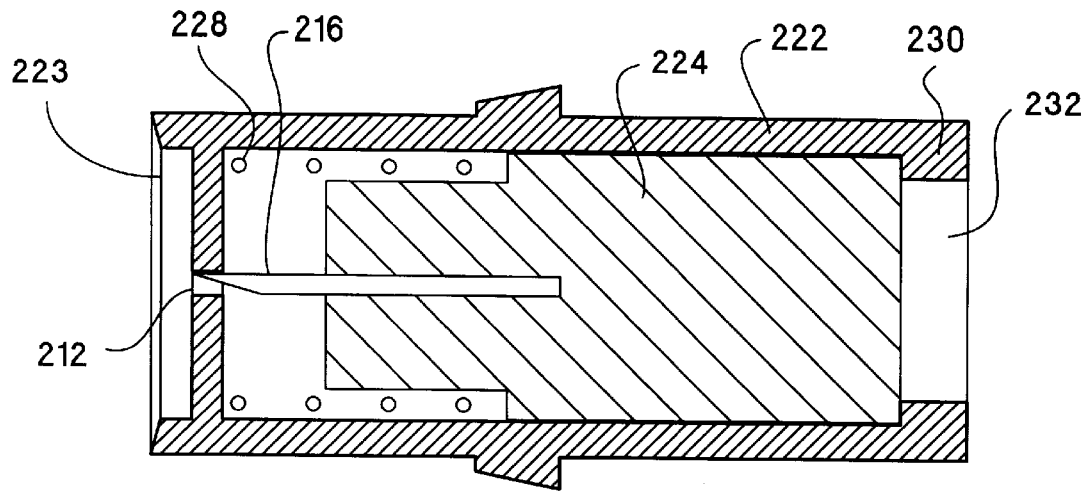
FIG. 3C shows a sectional view along the axis of the bar-shaped test cartridge of the present invention.
Figure 3D:
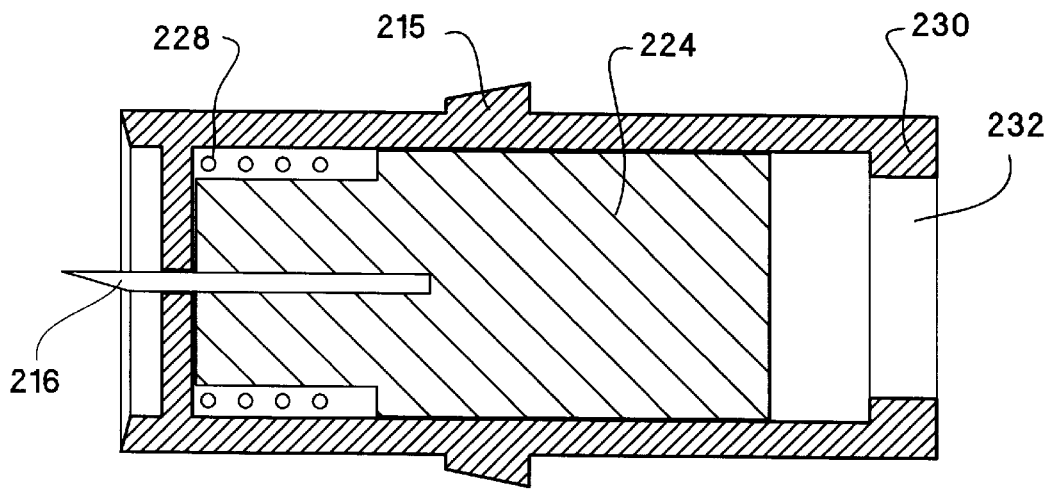
FIG. 3D shows a sectional view of the test cartridge of FIGS. 3A–3B, showing the lancet extended for lancing.

FIGS. 3C and 3D are sectional views of the test cartridge 210 along the plane C—C of FIG. 3A. Shown in FIGS. 3C and 3D (but not in FIG. 3B for clarity) is a retaining spring 228 which compresses the lancet mount 224 against the bottom 230 of the test cartridge 210. A large bore 232 on the bottom 230 of the cartridge case 222 permits an external actuator (not shown in FIGS. 3A to 3D) to extend through to act on the lancet mount 226. FIG. 3C shows the test cartridge 210 at rest, with the lancet 216 residing beneath the aperture 212 and the absorbent surface 218. When an external actuator (not shown) acts through the bottom bore 232 against the lancet mount 224, the cartridge spring 228 is compressed and lancet 216 will emerge through the aperture 212 where it can pierce a patient's skin. See FIG. 3D. When the actuator force is removed, e.g., by withdrawal of the actuator, the resilient nature of the cartridge retaining spring 228 returns the lancet 216 to the at-rest position inside the cartridge case 222. In this manner, the lancet 216 is only exposed during lancing. Therefore, the user is protected against unintentionally inflicted wounds and scratches, and also from exposure to the contaminated lancet. With prior technology, accidental lancet pricks can occur more easily.

In an alternative general embodiment, the previously described absorbent material is replaced with a small volume section that contains (1) the aperture for the lancet, and a passageway connecting this aperture to a test chamber that contains the active test area. The design of the aperture and passageway causes blood from the wound to be drawn into the test chamber by capillary action. Another embodiment has both the small volume section with test chamber described above and the absorbent material. However, in this embodiment, the absorbent material is not present near the wound where it could absorb blood immediately but rather a short distance away, e.g., on the side of the cartridge. Thus, the blood from the wound moves instead into the test chamber. The absorbent material in the vicinity provides the user with a convenient place to wipe the wound after testing.

Glucometer

Glucometer for Flat Type Test Cartridges

Figure 4:
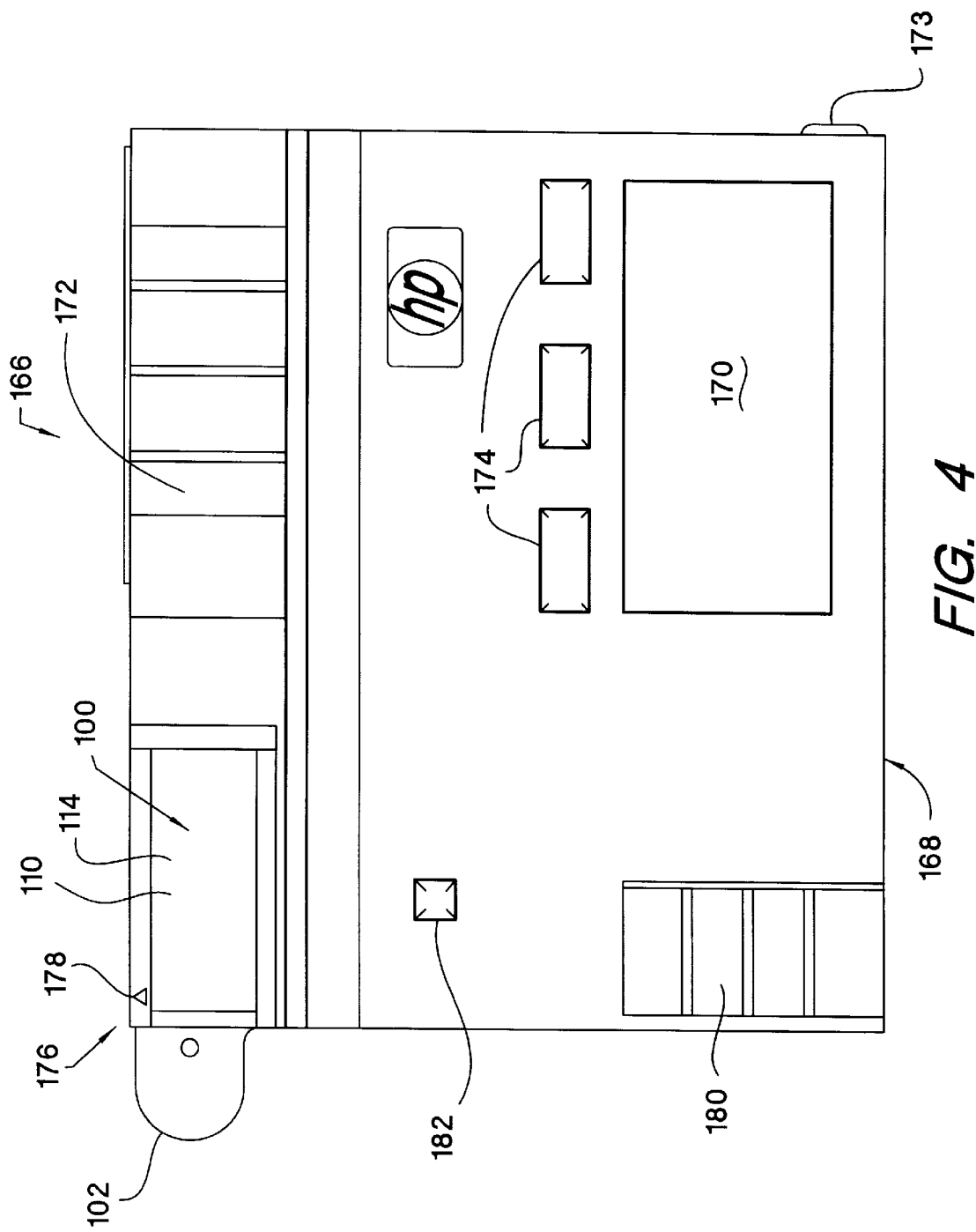
FIG. 4 shows a plan view of a glucometer suitable for use with a flat type test cartridge.

FIG. 4 shows a plan view of a glucometer in which a flat cartridge of FIG. 1 has been installed (or deployed). In this embodiment, the glucometer 166 has a body 168. A sweeper 172 in the glucometer can be used to sweep or push a single cartridge to deploy (or load) in a position for use. After use, the sweeper 172 can be used to push the used test cartridge out of the glucometer for disposal. Alternately, test cartridges may also be loaded or removed individually by finger.

As shown in FIG. 4, which shows a test cartridge 100 of FIG. 1 deployed, the test portion 102 (with the sample port 128 being most remote from the body 168) sticks out from the body. Additionally, preferably, the test cartridge 100 is loaded in the body of the glucometer 166 such that the test cartridge 100 has an exposed top surface 114 with an absorbent area 110 for wiping excess blood from the finger if necessary at the end of sampling and analyzing blood. Furthermore, a mark 178 can be molded or printed into the glucometer to show the location of the lancet hole 176 (corresponding to the location of the finger for lancing) through which the lancet will protrude to lance the skin of a patient.

To provide a driving (or actuating) force to push the lancet for lancing, an actuator 180, e.g., one that contains a sliding lever for cocking a spring-loaded activated (the spring and the puncher are not shown) puncher can be used. After cocking the spring in preparation for lancing, a button 182 can be pressed to release the spring-activated puncher to drive the pre-loaded lancet. As a result, the lancet tip is driven to extend out of the test cartridge 100. Spring actuated loading mechanisms are known in the art. The present spring-loaded actuator is similar to those found in existing lancing devices, but is integrated into this instrument housing. The lancing button 182 preferably is located away from the control buttons 174 and has a different color and markings for preventing it from being activated inadvertently. For example, the lancing button 182 can be located in a recess or inside a protective frame.

The body 168 of the glucometer 166 further has electronic circuits including a processor (which is not shown) to control and read the results of an analysis using the test cartridge. (A more detailed description of the instrument will follow). Analysis data and other information, e.g., date and time, can be displayed in a display 170 (e.g., LED or LCD display). The display can show the measured blood glucose concentration (e.g., in a large font for visually impaired users) and any information about the status of the measurement. The display may also show which cartridge is currently in the glucometer if the cartridge is coded. In the glucometer 166, electrical data port 173 enables electrical communication of data between the body 168 and external electronics, such as a remote computer, display unit, data storage, and the like. This data port 173 allows transfer of data out of (or into or both) the glucometer 166, e.g., past glucose readings stored in memory. The port may also load data, programs, or information from a physician's computer. Further, electronic connections can be present in the glucometer 166 to connect electrically the processor to electrical contacts in the test cartridge to permit electrical communication, including data and instruction transmission, between the test cartridge, and the processor. Control buttons 174 on the body 168 permit programming and set-up of the instrument (setting date, time, language preference, scrolling through stored values, on/off settings, instrument diagnostics, etc., as well as sending or receiving information to electronics external to the body).

To illustrate the use of the embodiment of the glucometer of FIG. 4, for example, a test cartridge 100 is loaded (or deployed) in the glucometer 166 and the spring-actuated driver is cocked to get the glucometer ready to lance a finger. When the cocked driver is released, the driver pushes the lancet to lance the finger.

A droplet of blood from the lancing wound can be exposed to sample port 128 and transferred to the test area 124 (not shown in FIG. 4) to be analyzed. Result of the analysis is transferred electrically through electrical contacts, wires, and connections to the processor. The control buttons 174 can be used to control the analysis of the blood sample, as well as to transfer information and data to external devices, e.g., computers, data storage, display, etc., through the data port 173. After analysis and data collection, the used test cartridge can be ejected.

For the flat test cartridge shown in FIGS. 2A and 2B, a glucometer similar to that shown in FIG. 4 can be used. That glucometer would have generally the same features as that of FIG. 4. When a flat test cartridge of FIGS. 2A and 2B is installed in the glucometer, the glucometer with the test cartridge would look like that of FIG. 4 except for the absence of the test portion 102 shown in FIG. 4. In the case of the FIG. 2A test cartridge, the test area 124B for receiving and analyzing blood is at the lancet exit port 133B. A glucometer suitable for use with the test cartridge of FIGS. 2A and 2B will be suitable for the test cartridge of FIG. 2C.

Glucometer for Bar-shaped Test Cartridges

An embodiment of a lancing device suitable for lancing with the bar-shaped test cartridge shown in FIG. 2A is shown in FIG. 5A and FIG. 5B. In this embodiment the lancing device has a generally elongated shape. FIGS. 5A and 5B show sectional views of the lancing device along the elongated dimension. The sectional views are sections through different angles (right angle to each other), so that they reveal different aspects of the interior parts. FIG. 5C is a schematic representation of the cross-section of the lancing device, showing line A-A as the plane for the sectional view of FIG. 5A and line B—B as the plane for the sectional view of FIG. 5B. This lancing device embodiment permits adjustment of the depth of the lancet and adjustment of the preload applied to the skin before lancing. In FIGS. 5A and 5B, the test cartridge 210 is shown removed from the lancing device 500 for clarity.

The lancing device 500 has a cartridge holder 502 with a recessed section 506 that accepts a bar-shaped test cartridge 210, similar to the bar-shaped test cartridge of FIG. 2A and FIG. 2B. The test cartridge 210 can be mounted in the cartridge holder 502 in a reproducible manner. That is, the test cartridge 210 can be repeatedly mounted and removed from the cartridge holder 502 and still attain the same position relative to the cartridge-by locating against a cartridge flange 215 which is molded onto the case 222 of the test cartridge 210. The bore 232 in the bottom of the test cartridge 210 is exposed to the interior of the lancing device through a bore 510 in the cartridge holder 502.

If the test cartridge 210 has an active test area for analytical measurement, then the test cartridge 210 should preferably also possess electrical contacts 519, which communicate to complementary contacts 523 in the cartridge holder 502. The lancing device 500 can either contain a processor such as CPU of a computer (not shown) or communicates with a CPU that can compute results from the signals received from the test cartridge. Thus, the lancing device 500 becomes part of an entire measurement instrument, which can compute and display results (such as blood glucose concentration).

The cartridge holder 502 can slide freely inside a casing 526. A force adjuster 528 can also slide freely inside the casing 526. The force adjuster 528 has a threaded end 530 that threads into matching threads on the cartridge holder 502. An adjuster spring 532 is compressed between the cartridge holder 502 and a flange 534 on the casing 526. By adjusting the position of the threaded end 530 of the force adjuster 528 relative to the threads on the cartridge holder 502, the degree of compression of the adjuster spring 532 can be adjusted, to apply an outward force on the cartridge holder 502 (and thereby also the force adjuster to which the cartridge holder is threaded). An adjuster flange 536 on the force adjuster 528 restrains the travel of the force adjuster (and cartridge holder 502) relative to the casing 526. Protruding further from the adjuster flange 536 on the force adjuster is a trigger 538, which extends to within a preset distance of a catch 540 on the casing 526. Inside the casing 526 is a plunger 542 having a larger base 544 and a long, more slender shaft 546. The base 544 has a small recession 548 and two protruding tabs 550. Attached to the plunger base 544 is a driving spring 552 which extends inside the casing 526 to the casing base 554. In equilibrium, the driving spring 552 holds the plunger 542 in the location shown in FIG. 5A (inside the casing) with the tip 556 of the plunger long shaft 546 held at a preset location inside the bore 510 of the cartridge holder 502. Around the casing 526 is a depth adjuster 560 and a cocking tube 562. One end of the cocking tube 562 has threads 564 that threadingly match into threads in the depth adjuster 560. Between the casing 526 and the cocking tube 562 (more specifically between the casing base 554 and the tube flange 566) is a tube spring 568 which applies a compressive force between the casing base 554 and the tube flange 566 on the cocking tube 562. The base (or closed end) 570 on the end of the cocking tube remote from the test cartridge 210 restrains the cocking tube 562 against the casing base 554.

The following describes the general steps of lancing with the lancing device of FIGS. 5A and 5B.

1. Load a test cartridge 210 in the cartridge holder 502.
2. Cock the lancing device 500 by pulling the cocking tube 562 back until the catch 540 on the casing 526 locks into the recession 548 on the plunger 546, thereby preloading (compressing) the driving spring 552. When the cocking tube 562 is pulled back in the proximal direction (away from the test cartridge 210), a cocking tube distal flange 572 pushes on the protruding tabs 550 of the plunger 542, thereby pushing the plunger 546 to compress the driving spring 552.
3. Release the cocking tube 562, thus allowing the force from the compressed tube spring 568 to return the cocking tube 562 to its earlier resting position.
4. Touch the intended site for lancing on the skin to the test cartridge 210 at its distal end. Continue to press the test cartridge 210 against the skin by pushing the entire lancing device 500. As a result, the cartridge holder 502 is compressed partially into the lancing device 500 against the force of the adjuster spring 532. At the same time the trigger 538 advances toward the catch 540 which retains the plunger 542.
5. At a predetermined location the trigger 538 releases the catch 540 from the plunger 542 and the driving spring 552 drives the plunger 542 distally, thereby forcing the lancet of the test cartridge into the skin. Afterwards, in the preferred mode in which the driving spring 552 is a ballistic spring that attaches to the plunger base 544, the driving spring recoils to its resting position and pulls back the plunger. As a result, the lancet retracts from the skin by the spring 228 in the test cartridge 210.

Alternatively, a conventional driver with a cocking and release mechanism including a release button can be used for driving the test cartridge. Such mechanisms with release buttons are known in the art.

The electrical contacts in the test cartridge 210 are in electrical communication with the electronics of the lancing device 500, which in turn is in electrical communication with electrical circuits, processors, displays, and the like that is applicable for analyzing, processing, or displaying of the results of analysis of blood in the test area. If preferred, such electronics, circuits, processors, and display can be incorporated in the lancing device 500 itself.

Details of lancing devices and glucometers suitable for using test cartridges for lancing is disclosed in the copending U.S. patent application Docket No. 10970332-1, entitled "Integrated System and Method for Blood Sampling and Analysis" (supra), said copending application has been incorporated by reference in its entirely herein. It is to be understood the test cartridges of the present invention can be used with glucometers not disclosed herein as long as proper a driving mechanism is provided to drive the lancing motion of lancets in the test cartridges.

Although the preferred embodiment of the present invention has been described and illustrated in detail, it is to be understood that a person skilled in the art can make modifications within the scope of the invention.

What is claimed is:

1. A cartridge for sampling blood from the skin of a patient, comprising:
    (a) a cartridge case having an opening through which an actuator can extend from outside the cartridge case thereinto, wherein the cartridge case includes two surfaces on opposite sides to facilitate stacking cartridges together such that one cartridge can be slid off from a stack of cartridges onto a supporting surface such that the one cartridge can be retained thereon while the lancet is actuated to extend the lancet tip outside the cartridge case for lancing;
    (b) a lancet having a tip for lancing the skin, housed in the cartridge case, the lancet being drivable by the actuator to transmit force to the lancet, thereby extending the lancet tip outside the cartridge case for lancing;
    (c) a spring inside the cartridge case associated with the lancet for applying a force to urge the lancet into the cartridge case when the lancet tip is extended outside the cartridge case; and
    (d) associated with the cartridge case, a compartment for receiving blood.

2. The cartridge according to claim 1 wherein the compartment includes an analytical region for analyzing the property of blood.

3. The cartridge according to claim 2 wherein the cartridge further comprises a reagent for interacting with blood to analyze the property of blood.

4. The cartridge according to claim 2 wherein the analytical region has a protective cover.

5. The cartridge according to claim 2 wherein the analytical region is proximate to the lancing opening for fluid communication between the analytical region and the opening.

6. The cartridge according to claim 1 further comprising a port associated with the cartridge case and within about 25 mm of the tip of the lancet when the lancet is extended for receiving blood from the skin after lancing, such that less than about 25 mm of relative movement of the lanced skin to the cartridge is needed to expose the port to the lanced skin, the port being in communication with the compartment via a channel which is capable of drawing blood therethrough by capillary forces.

7. The cartridge according to claim 1 wherein the cartridge further comprises an indicator mark on the cartridge case identifying a characteristic of the cartridge for visual identification.

8. The cartridge according to claim 1 wherein the cartridge further comprises an absorbent surface for wiping blood off the skin.

9. The cartridge according to claim 1 wherein the cartridge has no detachable cover shielding the lancet and wherein the cartridge case shields the lancet from being touched by the patient before being driven to extend, the lancet being returnable into the cartridge case after lancing the skin.

10. The cartridge according to claim 1 wherein the cartridge has at least a bar-shaped portion suitable for inserting into a bar-shaped storage slot and being expelled therefrom to associate with a driver or driving the lancet.

11. The cartridge according to claim 8 wherein the cartridge is disposable and is detachably held on the supporting surface for lancing.

12. The cartridge according to claim 1 wherein the compartment is optically accessible so its content or a portion thereof is visible to a user.

13. A blood sampling apparatus for sampling blood from the skin of a patient, comprising a cartridge which comprises:
    (a) a cartridge case having a lancing opening through which a lancet can extend therethrough and an opening for an actuator to extend from outside thereinto to urge the lancet toward the skin, wherein the cartridge case includes two surfaces on opposite sides to facilitate stacking cartridges together such that one cartridge can be slid off from a stack of cartridges onto a supporting surface such that the one cartridge can be retained thereon while the lancet is actuated to extend the lancet tip outside the cartridge case for lancing;
    (b) the lancet having a tip, housed in the cartridge case and operatively connected thereto such that the tip can be urged to extend through the lancing opening from the cartridge case for lancing the skin to yield blood, the lancet being returnable into the cartridge case by a spring in the cartridge case after lancing for safe disposal; and
    (c) an analytical region associated with the cartridge case and within about 25 mm of the tip of the lancet when the lancet is extended for receiving and analyzing blood from the skin after lancing, such that less than about 25 mm of relative movement of the lanced skin to the cartridge is needed to expose the analytical region to the lanced skin after lancing.

14. A method for sampling blood from the skin of a patient, comprising:
    (a) moving a cartridge from a stack of cartridges onto a support to be held thereon, the cartridge having a lancet having a tip and being shielded in the cartridge,
    (b) driving the lancet in the cartridge with an actuator extending from outside into the cartridge to extend the lancet tip out of a cartridge such that the lancet pierces the skin to yield blood;
    (c) urging the lancet back into the cartridge after lancing; and
    (d) depositing the blood yielded from skin to a compartment associated with the cartridge from which the lancet tip is extended.

15. The method according to claim 14, wherein the compartment has an analytical region for analysis of the blood.

16. The method according to claim 15, further including the step of exposing a site of the compartment to blood resulting from lancing the skin, wherein the site has a chemical reactive to blood.

17. The method according to claim 14 further comprising detachably holding the cartridge in a reusable driver for driving the lancet in the cartridge to lance the skin and further comprising detaching the cartridge from the driver for disposing the cartridge after use.

18. The method according to claim 14 wherein less than about 25 mm of movement of the lanced skin relative to the compartment is needed to expose an inlet of the compartment to blood from the lanced skin.

19. The method according to claim 17 further comprising deploying a cartridge in the driver before lancing and removing the cartridge after lancing, wherein the process from deploying to removing the cartridge is performed without requiring a protective shield covering the lancet tip to be detached from or attached to the cartridge.

20. The method according to claim 14 further comprising exposing a port on the cartridge to blood resulting from lancing the skin, wherein blood from the port can pass through a channel by capillary forces to the compartment.

21. The method according to claim 14, wherein the compartment has an inlet port proximate to the opening such that less than about 5 mm of relative movement of the cartridge to the lanced skin is needed to expose the inlet port to blood from the lanced skin.

22. The method according to claim 14, further comprising wiping blood off the skin on an absorbent surface on the cartridge.

23. A cartridge for sampling blood from the skin of a patient, comprising:
    (a) a cartridge case;
    (b) associated with the cartridge case, an absorbent surface for wiping blood off the skin; and
    (c) associated with the cartridge case, a compartment for receiving blood.

24. The cartridge according to claim 23 further comprising an opening in fluid communication with the compartment for blood intake from exterior and a cover covering the opening to shield the opening from contamination.

25. The cartridge according to claim 23 further comprising a site containing chemicals for non-combustional exothermic reaction.

26. A cartridge for sampling blood from the skin of a patient, comprising:
    (a) a cartridge case;
    (b) a lancet having a tip for lancing the skin, housed in the cartridge case; and
    (c) associated with the cartridge case, a compartment for receiving blood;
    wherein the cartridge has at least a bar-shaped portion suitable for inserting into a bar-shaped storage slot and being expelled therefrom to associate with a driver for driving the lancet.

27. A cartridge for sampling blood from the skin of a patient, comprising:
    (a) a cartridge case, including two surfaces on opposite sides thereof to facilitate stacking cartridges together in a stack such that one cartridge can be slid off the stack while the other cartridges in the stack are retained;
    (b) a lancet having a tip for lancing the skin, housed in the cartridge case; and
    (c) associated with the cartridge case, a compartment for receiving blood.

28. The cartridge according to claim 27, wherein the cartridge can be slid from a stack of cartridges onto a supporting surface such that the cartridge can be retained thereon while the lancet is actuated to extend the lancet tip outside the cartridge case for lancing.

29. A disposable cartridge for sampling blood from the skin of a patient, comprising:
    (a) a cartridge case, wherein the cartridge case includes two surfaces on opposite sides to facilitate stacking cartridges together such that one cartridge can be slid off from a stack of cartridges onto a supporting surface such that the one cartridge can be retained thereon while the lancet is actuated to extend the lancet tip outside the cartridge case for lancing;

(b) a lancet having a tip for lancing the skin, housed in the cartridge case, a spring associated with the lancet in the cartridge case for applying a force to urge the lancet tip back into the cartridge when the lancet tip is extended outside the cartridge case; and (c) associated with the cartridge case, a compartment for receiving blood.

30. The cartridge according to claim 23, further comprising a lancet having a tip, housed in the cartridge case, for lancing the skin when the tip is extended outside the cartridge case.

31. A cartridge for sampling blood from the skin of a patient, comprising:

(a) a cartridge case having an opening through which an actuator can extend from outside the cartridge case thereinto and a port associated with the cartridge case and within about 25 mm of the tip of the lancet when the lancet is extended for receiving blood from the skin after lancing, such that less than about 25 mm of relative movement of the lanced skin to the cartridge is needed to expose the port to the lanced skin, the port being in communication with the compartment via a channel which is capable of drawing blood therethrough by capillary forces;

(b) a lancet having a tip for lancing the skin, housed in the cartridge case, the lancet being drivable by the actuator to transmit force to the lancet, thereby extending the lancet tip outside the cartridge case for lancing;

(c) a spring inside the cartridge case associated with the lancet for applying a force to urge the lancet into the cartridge case when the lancet tip is extended outside the lancet case; and (d) associated with the cartridge case, a compartment for receiving blood.

32. The cartridge according to claim 31, wherein the port is at an opening through which the lancet extends through the cartridge case.

* * * * *